US 6,546,293 B2

United States Patent
Errico et al.

(10) Patent No.: US 6,546,293 B2
(45) Date of Patent: Apr. 8, 2003

(54) HOOK-SHAPED SPINAL CORD ELECTRODE ASSEMBLY HAVING A TELESCOPING ELECTRODE

(75) Inventors: Thomas J. Errico, Summit, NJ (US); Joseph P. Errico, Far Hills, NJ (US); Timothy J. Bortree, Summit, NJ (US)

(73) Assignee: Electro Core Technologies, LLC, Summit, NJ (US)

(*) Notice: Subject to any disclaimer, the term of this patent is extended or adjusted under 35 U.S.C. 154(b) by 0 days.

(21) Appl. No.: 09/789,937

(22) Filed: Feb. 15, 2001

(65) Prior Publication Data

US 2002/0111660 A1 Aug. 15, 2002

(51) Int. Cl.⁷ ................................................. A61N 1/05
(52) U.S. Cl. ...................................................... 607/117
(58) Field of Search ................................ 607/115, 116, 607/117, 58, 43

(56) References Cited

U.S. PATENT DOCUMENTS 6,163,727 A * 12/2000 Errico .......................... 607/117
6,175,769 B1 * 1/2001 Errico et al. ................. 607/117
6,233,488 B1 * 5/2001 Hess ............................ 607/117

* cited by examiner

Primary Examiner—Jiping Lu
(74) Attorney, Agent, or Firm—Joseph P. Errico, Esq.; Timothy J. Bortree, Esq.

(57) ABSTRACT

A spinal stimulation electrode assembly includes at least one wire lead having a proximal end adapted to couple to an electrical signal generator; a lamina hook having a blade hooking in a hooking direction; an electrode adapted to telescope from the blade in the hooking direction and having at least one electrical contact formed thereon that is electrically coupled to the wire lead; such that when the hook is disposed on a lamina of a spine and the electrode is telescoped from the blade, the electrical contact is positioned adjacent the spinal cord and an application of an electrical signal to the proximal end of the wire lead causes an electric potential to be applied to the spinal cord.

20 Claims, 3 Drawing Sheets

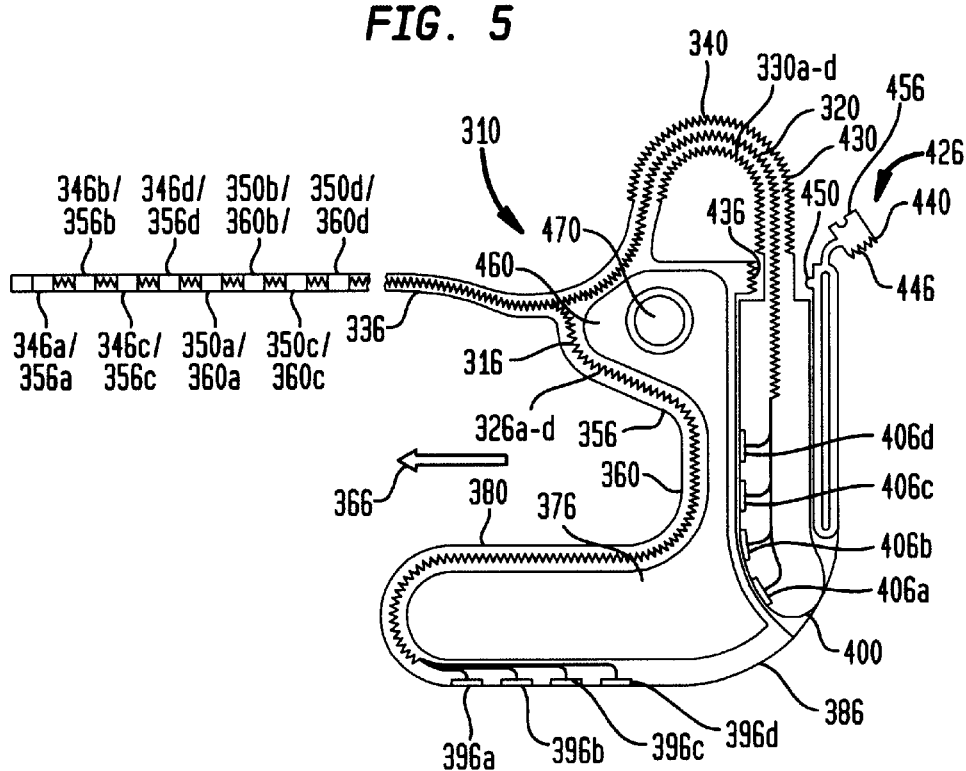
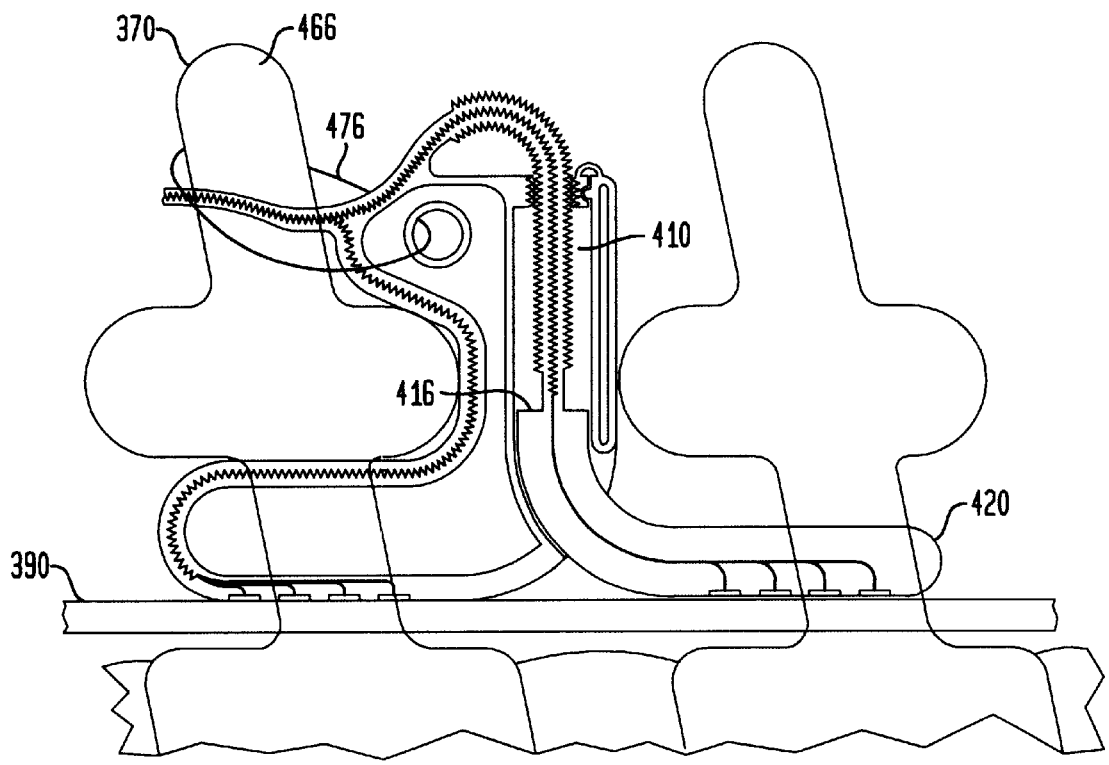

HOOK-SHAPED SPINAL CORD ELECTRODE ASSEMBLY HAVING A TELESCOPING ELECTRODE

FIELD OF THE INVENTION

This invention relates generally to a device used in the treatment of neurological disorders, especially pain and motor dysfunction by electro-stimulation of nerve fibers of the spinal cord, and more particularly to a novel combined assembly of an electrode and telescoping lamina hook that is more accurate in establishing a clinically effective placement of the electrode terminals, and more reliable in maintaining the position of the electrode itself, relative to the target fibers of the spinal cord and.

BACKGROUND OF THE INVENTION

The use of electrical stimulation for the purposes of alleviating pain and the treatment of other neurological afflictions has been utilized for a number of years, and in many instances has become the standard of care. In new applications, as well, electrical stimulation of components of the nervous system continues to show significant therapeutic promise.

More particularly, in the spine, the original approach to electrical stimulation was to place multiple electrical leads directly onto the dura around the spinal cord. In such a procedure, the laminae of a sequence of vertebrae were removed so that the leads could be placed in a spaced apart relation along the central posterior axis of the spinal cord. This approach required a substantially invasive procedure in which bones and tissue were displaced or removed. In addition, the high frequencies of electrode migration from the target site or sites rendered the entire procedure suspect.

Subsequent iterations of spinal cord stimulation devices were implanted much less invasively, generally by percutaneous positioning. The first generations of this approach were immediately advantageous over the prior methods, insofar as they were carried out using local anesthetic as the electrodes were guided into position with the use of a fluoroscope. These early non-invasive procedures continued to use single lead electrodes, thus requiring a plurality of separate implantations. In addition, the leads would still easily become dislodged and migrate from the desired treatment site, usually becoming ineffective, but sometimes having actively negative effects on other nerves. These limitations and failures associated with multiple implantations of single lead electrodes briefly caused a reversion to the older, more invasive approach.

In an attempt to unify the multiple leads necessary for spinal cord stimulation into a single electrode, thereby attempting to bring the state of the art back to non-invasive procedures, designs from the cardiovascular art, i.e., pacemakers, et al., were modified for use in the spine. Multiple lead electrodes had been used in the cardiovascular field for some time, and were generally designed to provide stimulation to a variety of points on the surface of the heart. The modifications of these leads included strengthening both the leads and the structure containing the leads for the stresses of the spine, reducing the diameter of the leads to a size more appropriate for use in the spine, and alternatively providing either a removable or permanent rigid wire within the electrode to enhance placement. Unfortunately, while eliminating some of the causes associated with electrode migration, and reducing the number of electrodes which could migrate, the advances did not address the fundamental inability to fix the electrode at the appropriate location. This problem has been, and continues to be a significant drawback to the use of spinal cord stimulation in the regular treatment of pain.

Accordingly, there is a need to provide a spinal cord stimulator assembly that increases the accuracy of the placement of the electrode terminals and reduces the incidence and complications associated with the migration of the electrode.

SUMMARY OF THE INVENTION

The invention provides electrode assemblies for use in spinal cord stimulation that may be used in conjunction with standard and/or advanced electrical signal sources. Each of the electrode assemblies has at least one telescoping electrode that increases the accuracy of the placement of electrode contacts along a spinal cord, and a hook structure that reduces the incidence of, and complications associated with, the migration of the electrode. A variety of different embodiments of the invention are contemplated, exemplary ones of which are disclosed herein.

In a first embodiment, the invention includes a spinal stimulation electrode assembly including at least one wire lead having a proximal end adapted to couple to an electrical signal generator; a lamina hook having a blade hooking in a hooking direction; an electrode adapted to telescope from the blade in the hooking direction and having at least one electrical contact formed thereon that is electrically coupled to the wire lead; such that when the hook is disposed on a lamina of a spine and the electrode is telescoped from the blade, the electrical contact is positioned adjacent the spinal cord and an application of an electrical signal to the proximal end of the wire lead causes an electric potential to be applied to the spinal cord.

In an aspect of the invention, the blade has a bore extending therethrough and the electrode is adapted to telescope from the bore.

In another aspect of the invention, the assembly further comprises an electrode lock that can be used to lock the electrode in a telescoped position. The electrode lock can comprise a rough surface on the electrode, a rough surface on the bore, and a cap having a rough surface that frictionally engages the electrode's rough surface and causes the bore's rough surface to frictionally engage the electrode's rough surface when the cap is closed.

In yet another aspect of the invention, the hook further comprises a head that can be used to couple the hook to a bone of the spine when the hook is disposed on the lamina. The head can accordingly include a hole through which a wire may be passed and tied to the bone.

The wire lead can comprise a plurality of wire leads and can be encased in an insulating and flexible elastomeric sheath; the electrical contact can comprise a plurality of electrical contacts; and the hook can comprise an insulating and flexible elastomeric coating.

In a second embodiment, the invention includes first and second wire leads each having a proximal end adapted to couple to an electrical signal generator; a lamina hook having a blade hooking in a hooking direction; a first electrode adapted to telescope from the blade in the hooking direction and having at least one electrical contact formed thereon that is electrically coupled to the first wire lead; a second electrode adapted to telescope from the blade in an opposite direction from the hooking direction and having at least one electrical contact formed thereon that is electrically coupled to the second wire lead; such that when the hook is disposed on a lamina of the spine and the first and second electrodes are telescoped from the blade, the electrical contacts are positioned adjacent the spinal cord and an application of electrical signals to the proximal ends of the wire leads causes electric potentials to be applied to the spinal cord.

In an aspect of the invention, the blade has a forked bore extending therethrough and the first electrode is adapted to telescope from a first branch of the bore and the second electrode is adapted to telescope from a second branch of the bore.

In another aspect of the invention, the assembly further comprises an electrode lock that can be used to lock the electrodes in their respective telescoped positions. The electrode lock can comprise a rough surface on the first electrode, a rough surface on the second electrode, a rough surface on the bore, and a cap having a rough surface that frictionally engages one of the rough surfaces of the electrodes and causes the bore's rough surface to frictionally engage the other of the rough surfaces of the electrodes, and the rough surfaces of the electrodes to frictionally engage one another when the cap is closed.

In yet another aspect of the invention, the hook further comprises a head that can be used to couple the hook to a bone of the spine when the hook is disposed on the lamina. The head can accordingly include a hole through which a wire may be passed and tied to the bone.

Each of the first wire lead and the second wire lead can comprise a plurality of wire leads and can be encased in an insulating and flexible elastomeric sheath; each of the electrical contact of the first electrode and the electrical contact of the second electrode can comprise a plurality of electrical contacts; and the hook can comprise an insulating and flexible elastomeric coating.

In a third embodiment, the invention includes first and second wire leads each having a proximal end adapted to couple to an electrical signal generator; a lamina hook having a blade hooking in a hooking direction, the blade having an undersurface that seats adjacent to a spinal cord when the hook is disposed on a lamina of a spine, the undersurface having at least one electrical contact formed thereon that is electrically coupled to the first wire lead; an electrode adapted to telescope from the blade in an opposite direction from the hooking direction and having at least one electrical contact formed thereon that is electrically coupled to the second wire lead; such that when the hook is disposed on a lamina of a spine and the electrode is telescoped from the blade, the electrical contacts are positioned adjacent the spinal cord and an application of electrical signals to the proximal ends of the wire leads causes electric potentials to be applied to the spinal cord.

In an aspect of the invention, the blade has a bore extending therethrough and the electrode is adapted to telescope from the bore.

In another aspect of the invention, the assembly further comprises an electrode lock that can be used to lock the electrode in a telescoped position. The electrode lock can comprise a rough surface on the electrode, a rough surface on the bore, and a cap having a rough surface that frictionally engages the electrode's rough surface and causes the bore's rough surface to frictionally engage the electrode's rough surface when the cap is closed.

In yet another aspect of the invention, the hook further comprises a head that can be used to couple the hook to a bone of the spine when the hook is disposed on the lamina. The head can accordingly include a hole through which a wire may be passed and tied to the bone.

Each of the first wire lead and the second wire lead can comprise a plurality of wire leads and can be encased in an insulating and flexible elastomeric sheath; each of the electrical contact of the undersurface and the electrical contact of the electrode can comprise a plurality of electrical contacts; and the hook can comprise an insulating and flexible elastomeric coating.

BRIEF DESCRIPTION OF THE DRAWINGS

FIG. 5 is a side cross-section view of a third embodiment of an electrode assembly of the invention.

FIG. 6 is a side cross-section view of the embodiment of FIG. 5 mounted between laminae of a spine and showing a telescoped electrode.

DETAILED DESCRIPTION OF THE INVENTION

While the invention will be described more fully hereinafter with reference to the accompanying drawings, in which particular embodiments are shown, and with respect to methods of implantation, it is to be understood that persons skilled in the art may modify the invention while achieving the functions and results of the invention. Accordingly, the descriptions are to be understood as illustrative and exemplary of specific structures, aspects and features within the broad scope of the invention and not as limiting of such broad scope. Like numbers refer to similar features of like elements throughout.

Figure 1:
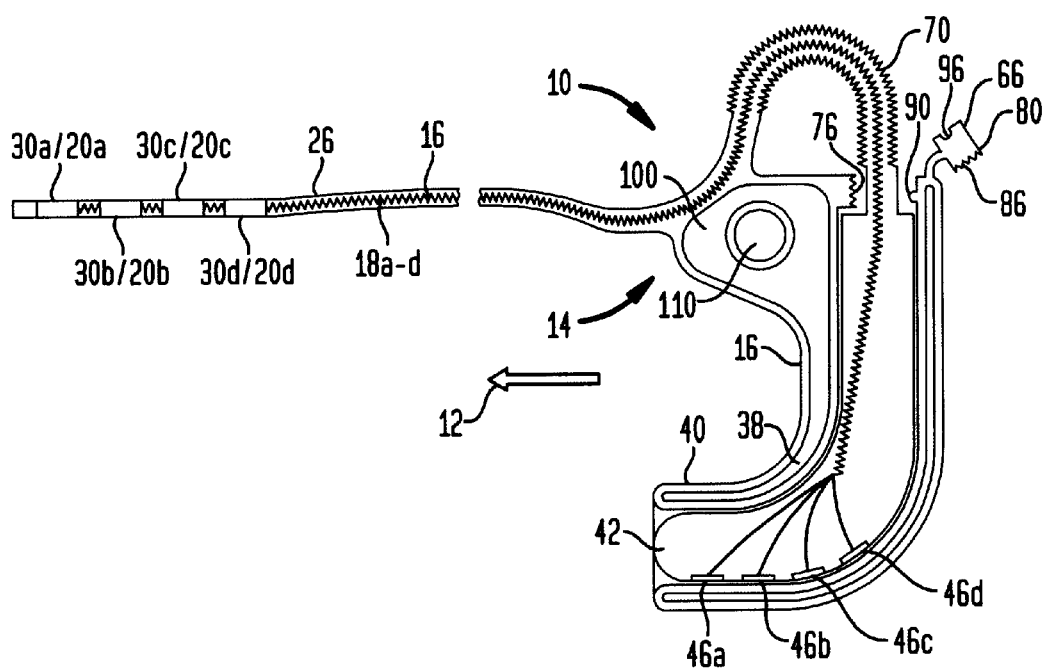
FIG. 1 is a side cross-section view of a first embodiment of an electrode assembly of the invention.
Figure 2:
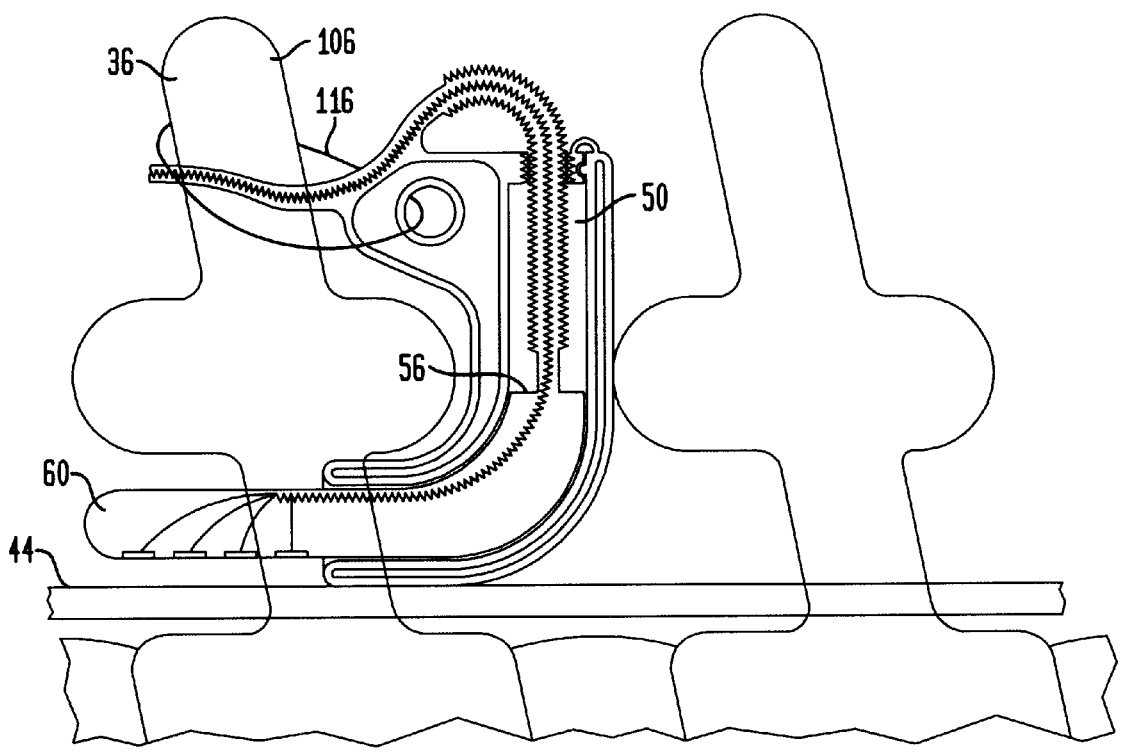
FIG. 2 is a side cross-section view of the embodiment of FIG. 1 mounted to a lamina of a spine and showing a telescoped electrode.

Referring now to FIGS. 1–2, a first embodiment of the invention includes a spinal cord stimulation electrode assembly 10 including at least one wire lead 16. The wire lead 16 can be a plurality of wire leads 18a–d that are wound in tight helices and insulated from one another so each may carry a different electrical potential. The wire leads 18a–d can be encased in a sheath 26 that is formed from an elastomeric, insulating and flexible material that allows the sheath 26 to be manipulated in the axial and transverse direction, minimizes the destructive deformation of the wire leads 18a–d during movement, and insulates the wire leads 18a–d from one another and from the exterior of the sheath 26. Although not shown, a rigid wire may be slideably inserted into and removed from the sheath 26 by the surgeon to provide rigidity that may be necessary during implantation of the electrode assembly. Each of the wire leads 18a–d is coupled to a corresponding terminal 30a–d at a proximal end 20a–d of the respective wire lead. The portion of the sheath 26 containing the terminals 30a–d can be any suitable cross-sectional shape. A cylindrical cross-sectional shape is preferred and the terminals 30a–d can be circumferential contacts surrounding the sheath, each forming an electrical contact band. Alternatively, the portion of the sheath 26 containing the terminals 30a–d can be flattened out to form a thin ribbon-like structure. In either conformation, the terminals 30a–d are preferably spaced apart so they are in electrical isolation from one another. The portion of the sheath 26 containing the terminals 30a–d can be coupled to corresponding terminals of an electrical signal generator (not shown) that can deliver electrical potentials to the terminals 30a–d. The generator can be implanted, or can be external to the patient's body and the wire leads 18a–d can extend transcutaneously to it.

The assembly further includes a lamina hook 14 having a blade 16 hooking in a hooking direction denoted by arrow 12. When the hook 14 is disposed on a lamina 36 of a vertebral bone, the blade 16 cups a lateral edge of the lamina 36 as best shown in FIG. 2. The internal structure 38 of the hook 14 preferably includes a rigid material, such as a hard plastic, that maintains the integrity of the hook shape. While the rigid material is preferably non-conductive, it can be a conductive material such as metal if precautions are taken to ensure that the wire leads 18a–d do not electrically contact it. The hook 14 preferably has a coating 40 of an elastomeric material to prevent damage to surrounding tissue when the hook 14 is disposed on the lamina 36.

The assembly further includes an electrode 42 adapted to telescope from the blade 16 in the hooking direction as best shown in FIG. 2. The electrode 42 has at least one and preferably a plurality of electrical contacts 46a–d formed thereon that are respectively electrically coupled to the wire leads 18a–d and therefore can be coupled to different voltages within the electrical signal generator (not shown). The number and position of the contacts on the electrode 42 can be selected from a nearly infinite variety. Four contacts 46a–d in a linear series are shown, but any number of pads in opposing pairs or staggered pairs could be appropriate in certain clinical applications. The contacts 46a–d and their relative position determine the distribution of electric potentials through the tissue against which the contacts 46a–d are placed. The current causes the disruption of pain signals in the target nerve roots and thereby alleviates pain or other suitably treatable disorder.

To permit the accurate positioning of the contacts 46a–d, the electrode 42 can preferably be variably telescoped from the blade 16 in the hooking direction. That is, when the hook 14 is disposed on the lamina 36, the surgeon is preferably able to variably telescope the electrode 42 from the blade 16 until the electrical contacts 46a–d are properly positioned adjacent the spinal cord 44. For example, a clinical application may require the electrode 42 to be partially telescoped from the blade 16, while another clinical application may require the electrode 42 to be almost fully telescoped from the blade 16. Other clinical applications may require other telescoped positions of the electrode 42. When the hook 14 is so disposed and the electrode 42 is positioned, the electrical contacts 46a–d are positioned adjacent the spinal cord 44 and an application of an electrical signal to the proximal ends 20a–d of the wire leads 18a–d causes an electric potential to be applied to the spinal cord 44 to achieve the desired clinical result.

In the embodiment shown in FIGS. 1–2, the telescoping function is provided by the blade 16 having a bore 50 extending therethrough and the electrode 42 being adapted to telescope from the bore 50. More specifically, applying a force to a first end 56 of the electrode 42 causes a second end 60 to telescope from the bore 50. The electrode 42 can be formed of an elastomeric material that is flexible to permit the electrode to navigate the curve of the bore 50 as it is telescoped from the bore 50. The elastomeric material can also support the wire leads 18a–d and the electrical contacts 46a–d.

To maintain the accurate positioning of the contacts 46a–d, the assembly further includes an electrode lock 66 that can be used to lock the electrode 42 in a telescoped position. In the embodiment shown in FIGS. 1–2, the electrode lock 66 includes a rough surface 70 on the electrode 42, a rough surface 76 on the bore 50, and a cap 80 having a rough surface 86 that frictionally engages the electrode's rough surface 70 and causes the bore's rough surface 76 to frictionally engage the electrode's rough surface 70 when the cap 80 is closed as best shown in FIG. 2. Applying pressure to the cap 80 to close the cap 80 compresses the electrode's rough surface 70 between the bore's rough surface 76 and the cap's rough surface 86 and snaps a securing protrusion 90 on the bore 50 within a corresponding securing notch 96 on the cap 80. When the cap 80 is so closed, the electrode 42 cannot be retreated into or further telescoped from the bore 50 because the rough surfaces are frictionally engaged by the compression.

To secure the hook 14 to the lamina 36, the assembly further includes a head 100 that can be used to couple the hook 14 to a bone 106 of the spine, such as the spinous process, when the hook 14 is disposed on the lamina 36. Securing the hook 14 prevents it from becoming dislodged, translating or sliding in a way that moves the electrical contacts 46a–d away from their positions. In the embodiment shown in FIGS. 1–2, the head 100 includes a hole 110 that extends transverse to the axes of the head 100 and the blade 16 and through which a wire 116, such as a surgical wire, may be passed and tied to the bone 106 as shown.

Figure 3:
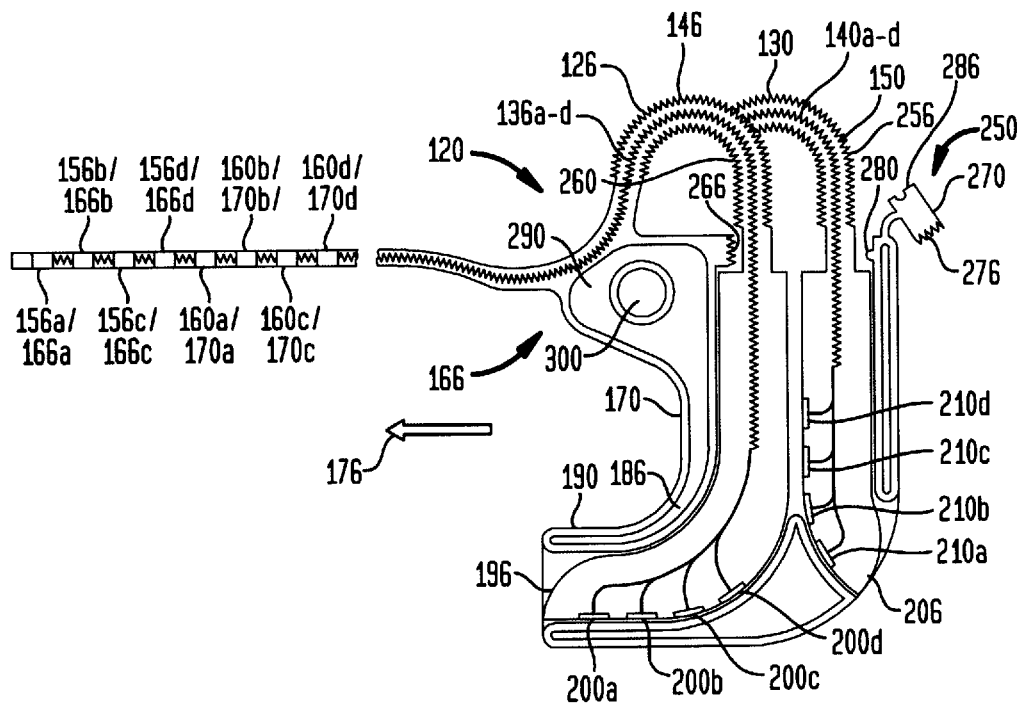
FIG. 3 is a side cross-section view of a second embodiment of an electrode assembly of the invention.
Figure 4:
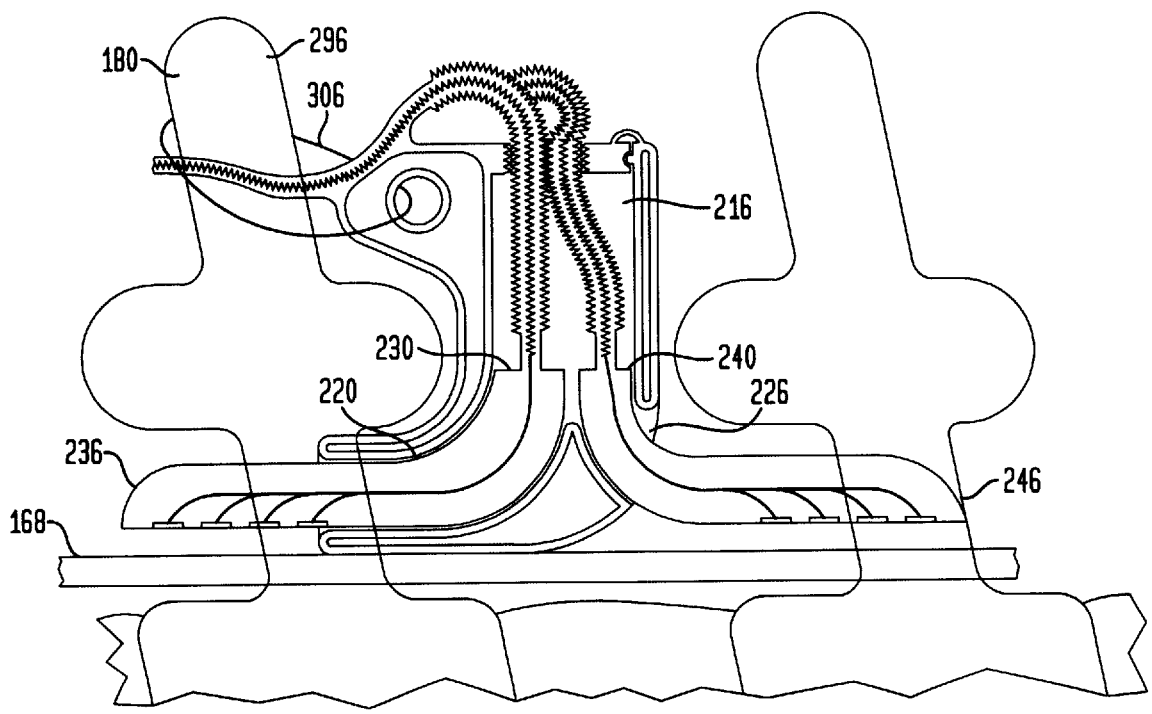
FIG. 4 is a side cross-section view of the embodiment of FIG. 3 mounted between adjacent laminae of a spine and showing telescoped electrodes.

Referring now to FIGS. 3–4, a second embodiment of the invention includes a spinal cord stimulation electrode assembly 120 including a first wire lead 126 and a second wire lead 130. Each of the first and second wire leads 126, 130 can be a plurality of wire leads 136a–d, 140a–d that are wound in tight helices and insulated from one another so each may carry a different electrical potential. The wire leads 136a–d, 140a–d can be encased in a respective sheath 146, 150 that is formed from an elastomeric, insulating and flexible material that allows the sheath 146, 150 to be manipulated in the axial and transverse direction, minimizes the destructive deformation of the wire leads 136a–d, 140a–d during movement, and insulates the wire leads 136a–d, 140a–d from one another and from the exterior of the respective sheath 146, 150. Although not shown, a rigid wire may be slideably inserted into and removed from the sheath 146, 150 by the surgeon to provide rigidity that may be necessary during implantation of the electrode assembly. Each of the wire leads 136a–d, 140a–d is coupled to a corresponding terminal 156a–d, 160a–d at a proximal end 166a–d, 170a–d of the respective wire lead. The portion of each sheath 146, 150 containing the respective terminals 156a–d, 160a–d can be any suitable cross-sectional shape. A cylindrical cross-sectional shape is preferred and the terminals 156a–d, 160a–d can be circumferential contacts surrounding the sheath 146, 150, each forming an electrical contact band. Alternatively, the portion of each sheath 146, 150 containing the respective terminals 156a–d, 160a–d can be flattened out to form a thin ribbon-like structure. In either conformation, the terminals 156a–d, 160a–d are preferably spaced apart so they are in electrical isolation from one another. The portion of each sheath 146, 150 containing the terminals 156a–d, 160a–d can be coupled to corresponding terminals of an electrical signal generator (not shown) that can deliver electrical potentials to the terminals 156a–d, 160a–d. The generator can be implanted, or can be external to the patient's body and the wire leads 136a–d, 140a–d can extend transcutaneously to it.

The assembly further includes a lamina hook 166 having a blade 170 hooking in a hooking direction denoted by arrow 176. When the hook 166 is disposed on a lamina 180 of a vertebral bone, the blade 170 cups a lateral edge of the lamina 180 as best shown in FIG. 4. The internal structure 186 of the hook 166 preferably includes a rigid material, such as a hard plastic, that maintains the integrity of the hook shape. While the rigid material is preferably non-conductive, it can be a conductive material such as metal if precautions are taken to ensure that the wire leads 136a–d, 140a–d do not electrically contact it. The hook 166 preferably has a coating 190 of an elastomeric material to prevent damage to surrounding tissue when the hook 166 is disposed on the lamina 180.

The assembly further includes a first electrode 196 adapted to telescope from the blade 170 in the hooking direction as best shown in FIG. 4. The first electrode 196 has at least one and preferably a plurality of electrical contacts 200a–d formed thereon that are respectively electrically coupled to the wire leads 136a–d and therefore can be coupled to different voltages within the electrical signal generator (not shown). The number and position of the contacts on the first electrode 196 can be selected from a nearly infinite variety. Four contacts 200a–d in a linear series are shown, but any number of pads in opposing pairs or staggered pairs could be appropriate in certain clinical applications. The contacts 200a–d and their relative position determine the distribution of electric potentials through the tissue against which the contacts 200a–d are placed. The current causes the disruption of pain signals in the target nerve roots and thereby alleviates pain or other suitably treatable disorder.

The assembly further includes a second electrode 206 adapted to telescope from the blade 170 in an opposite direction from the hooking direction as best shown in FIG. 4. The second electrode 206 has at least one and preferably a plurality of electrical contacts 210a–d formed thereon that are respectively electrically coupled to the wire leads 140a–d and therefore can be coupled to different voltages within the electrical signal generator (not shown). The number and position of the contacts on the second electrode 206 can be selected from a nearly infinite variety. Four contacts 210a–d in a linear series are shown, but any number of pads in opposing pairs or staggered pairs could be appropriate in certain clinical applications. The contacts 210a–d and their relative position determine the distribution of electric potentials through the tissue against which the contacts 210a–d are placed. The current causes the disruption of pain signals in the target nerve roots and thereby alleviates pain or other suitably treatable disorder.

To permit the accurate positioning of the contacts 200a–d, 210a–d, the first electrode 196 can preferably be variably telescoped from the blade 170 in the hooking direction and the second electrode 206 can be variably telescoped from the blade 170 in the opposite direction from the hooking direction. That is, when the hook 166 is disposed on the lamina 180, the surgeon is preferably able to variably telescope the first electrode 196 from the blade 170 until the electrical contacts 200a–d are properly positioned adjacent the spinal cord 168. Similarly, when the hook 166 is disposed on the lamina 180, the surgeon is preferably able to variably telescope the second electrode 206 from the blade 170 until the electrical contacts 210a–d are properly positioned adjacent the spinal cord 168. For example, a clinical application may require the first electrode 196 to be partially telescoped from the blade 170 and the second electrode 206 to be almost fully telescoped from the blade 170. Another clinical application may require both the first electrode 196 and the second electrode 206 to be partially telescoped from the blade 170. Other clinical applications may require other telescoped positions of the electrodes 196, 206. When the hook 166 is so disposed and the electrodes 196, 206 are positioned, the electrical contacts 200a–d, 210a–d are positioned adjacent the spinal cord 168 and an application of an electrical signal to the proximal ends 166a–d, 170a–d of the wire leads 136a–d, 140a–d causes an electric potential to be applied to the spinal cord 168 to achieve the desired clinical result.

In the embodiment shown in FIGS. 3–4, the telescoping function is provided by the blade 170 having a forked bore 216 extending therethrough, the first electrode 196 being adapted to telescope from a first branch 220 of the bore 216, and the second electrode 206 being adapted to telescope from a second branch 226 of the bore 216. More specifically, applying a force to a first end 230 of the first electrode 196 causes a second end 236 to telescope from the bore 216. Similarly, applying a force to a first end 240 of the second electrode 206 causes a second end 246 to telescope from the bore 216. The electrodes 196, 206 can be formed of an elastomeric material that is flexible to permit the electrodes 196, 206 to navigate the curve of their respective branch 220, 226 of the bore 216 as they are telescoped from the bore 216. The elastomeric material can also support the wire leads 136a–d, 140a–d and the electrical contacts 200a–d, 210a–d.

To maintain the accurate positioning of the contacts 200a–d, 210a–d. assembly further includes an electrode lock 250 that can be used to lock the electrodes 196, 206 in their telescoped positions. In the embodiment shown in FIGS. 3–4, the electrode lock 250 includes a rough surface 256 on the first electrode 196, a rough surface 260 on the second electrode 206, a rough surface 266 on the bore 216, and a cap 270 having a rough surface 276 that frictionally engages the second electrode's rough surface 260 and causes the second electrode's rough surface 260 to frictionally engage the first electrode's rough surface 256 and the bore's rough surface 266 to frictionally engage the first electrode's rough surface 256 when the cap 270 is closed as best shown in FIG. 4. Applying pressure to the cap 270 to close the cap 270 compresses the electrodes' rough surfaces 256, 260 against one another and between the bore's rough surface 266 and the cap's rough surface 276 and snaps a securing protrusion 280 on the bore 216 within a corresponding securing notch 286 on the cap 270. When the cap 270 is so closed, the electrodes 196, 206 cannot be retreated into or further telescoped from the bore 216 because the rough surfaces are frictionally engaged by the compression.

To secure the hook 166 to the lamina 180, the assembly further includes a head 290 that can be used to couple the hook 166 to a bone 296 of the spine, such as the spinous process, when the hook 166 is disposed on the lamina 180. Securing the hook 166 prevents it from becoming dislodged, translating or sliding in a way that moves the electrical contacts 200a–d, 210a–d away from their positions. In the embodiment shown in FIGS. 3–4, the head 290 includes a hole 300 that extends transverse to the axes of the head 290 and the blade 170 and through which a wire 306, such as a surgical wire, may be passed and tied to the bone 296 as shown.

Referring now to FIGS. 5–6, a third embodiment of the invention includes a spinal cord stimulation electrode assembly 310 including a first wire lead 316 and a second wire lead 320. Each of the first and second wire leads 316, 320 can be a plurality of wire leads 326a–d, 330a–d that are wound in tight helices and insulated from one another so each may carry a different electrical potential. The wire leads 326a–d, 330a–d can be encased in a respective sheath 336, 340 that is formed from an elastomeric, insulating and flexible material that allows the sheath 336, 340 to be manipulated in the axial and transverse direction, minimizes the destructive deformation of the wire leads 326a–d, 330a–d during movement, and insulates the wire leads 326a–d, 330a–d from one another and from the exterior of the respective sheath 336, 340. Although not shown, a rigid wire may be slideably inserted into and removed from the sheath 336, 340 by the surgeon to provide rigidity that may be necessary during implantation of the electrode assembly. Each of the wire leads 326a–d, 330a–d is coupled to a corresponding terminal 346a–d, 350a–d at a proximal end 356a–d, 360a–d of the respective wire lead. The portion of each sheath 336, 340 containing the respective terminals 346a–d, 350a–d can be any suitable cross-sectional shape. A cylindrical cross-sectional shape is preferred and the terminals 346a–d, 350a–d can be circumferential contacts surrounding the sheath 336, 340, each forming an electrical contact band. Alternatively, the portion of each sheath 336, 340 containing the respective terminals 346a–d, 350a–d can be flattened out to form a thin ribbon-like structure. In either conformation, the terminals 346a–d, 350a–d are preferably spaced apart so they are in electrical isolation from one another. The portion of each sheath 336, 340 containing the terminals 346a–d, 350a–d can be coupled to corresponding terminals of an electrical signal generator (not shown) that can deliver electrical potentials to the terminals 346a–d, 350a–d. The generator can be implanted, or can be external to the patient's body and the wire leads 18a–d can extend transcutaneously to it.

The assembly further includes a lamina hook 356 having a blade 360 hooking in a hooking direction denoted by arrow 366. When the hook 356 is disposed on a lamina 370 of a vertebral bone, the blade 360 cups a lateral edge of the lamina 370 as best shown in FIG. 6. The internal structure 376 of the hook 356 preferably includes a rigid material such as a hard plastic, that maintains the integrity of the hook shape. While the rigid material is preferably non-conductive, it can be a conductive material such as metal if precautions are taken to ensure that the wire leads 326a–d, 330a–d do not electrically contact it. The hook 356 preferably has a coating 380 of an elastomeric material to prevent damage to surrounding tissue when the hook 356 is disposed on the lamina 370.

The blade 360 has an undersurface 386 that seats adjacent to a spinal cord 390 when the hook 356 is disposed on the lamina 370. The undersurface 386 has at least one and preferably a plurality of electrical contacts 396a–d formed thereon that are electrically coupled to the wire leads 326a–d and therefore can be coupled to different voltages within the electrical signal generator (not shown). The wire leads 326a–d can extend through the coating 380 to be insulated from one another and from the internal structure 376 of the hook 356 as necessary.

The assembly further includes an electrode 400 adapted to telescope from the blade 360 in an opposite direction from the hooking direction as best shown in FIG. 6. The electrode 400 has at least one and preferably a plurality of electrical contacts 406a–d formed thereon that are respectively electrically coupled to the wire leads 330a–d and therefore can be coupled to different voltages within the electrical signal generator (not shown).

The number and position of the contacts 396a–d, 406a–d can be selected from a nearly infinite variety. Four contacts in a linear series are shown, but any number of pads in opposing pairs or staggered pairs could be appropriate in certain clinical applications. The contacts 396a–d, 406a–d and their relative position determine the distribution of electric potentials through the tissue against which the contacts 396a–, d 406a–d are placed. The current causes the disruption of pain signals in the target nerve roots and thereby alleviates pain or other suitably treatable disorder.

To permit the accurate positioning of the contacts 406a–d, the electrode 400 can preferably be variably telescoped from the blade 360 in the opposite direction from the hooking direction. That is, when the hook 356 is disposed on the lamina 370, the surgeon is preferably able to variably telescope the electrode 400 from the blade 360 until the electrical contacts 406a–d are properly positioned adjacent the spinal cord 390. For example, a clinical application may require the electrode 400 to be partially telescoped from the blade 360, while another clinical application may require the electrode 400 to be almost fully telescoped from the blade 360. Other clinical applications may require other telescoped positions of the electrode 400.

When the hook 356 is so disposed, the electrical contacts 396a–d are positioned adjacent the spinal cord 390. Further, when the electrode 400 is positioned, the electrical contacts 406a–d are positioned adjacent the spinal cord 390. Thereafter, when an application of an electrical signal to the proximal ends 356a–d, 360a–d of the wire leads 326a–d, 330a–d causes an electric potential to be applied to the spinal cord 390 to achieve the desired clinical result.

In the embodiment shown in FIGS. 5–6, the telescoping function is provided by the blade 360 having a bore 410 extending therethrough and the electrode 400 being adapted to telescope from the bore 410. More specifically, applying a force to a first end 416 of the electrode 400 causes a second end 420 to telescope from the bore 410. The electrode 400 can be formed of an elastomeric material that is flexible to permit the electrode 400 to navigate the curve of the bore 410 as it is telescoped from the bore 410. The elastomeric material can also support the wire leads 330a–d and the electrical contacts 406a–d.

To maintain the accurate positioning of the contacts 406a–d, the assembly further includes an electrode lock 426 that can be used to lock the electrode 400 in a telescoped position. In the embodiment shown in FIGS. 5–6, the electrode lock 426 includes a rough surface 430 on the electrode 400, a rough surface 436 on the bore 410, and a cap 440 having a rough surface 446 that frictionally engages the electrode's rough surface 430 and causes the bore's rough surface 436 to frictionally engage the electrode's rough surface 430 when the cap 440 is closed as best shown in FIG. 6. Applying pressure to the cap 440 to close the cap 440 compresses the electrode's rough surface 430 between the bore's rough surface 436 and the cap's rough surface 446 and snaps a securing protrusion 450 on the bore 410 within a corresponding securing notch 456 on the cap 440. When the cap 440 is so closed, the electrode 400 cannot be retreated into or further telescoped from the bore 410 because the rough surfaces are frictionally engaged by the compression.

To secure the hook 356 to the lamina 370, the assembly further includes a head 460 that can be used to couple the hook 356 to a bone 466 of the spine, such as the spinous process, when the hook 356 is disposed on the lamina 370. Securing the hook 356 prevents it from becoming dislodged, translating or sliding in a way that moves the electrical contacts 326a–d, 330a–d away from their positions. In the embodiment shown in FIGS. 5–6, the head 460 includes a hole 470 that extends transverse to the axes of the head 460 and the blade 360 and through which a wire 476, such as a surgical wire, may be passed and tied to the bone 466 as shown.

While there has been described and illustrated specific embodiments of new and novel electrical stimulation implant devices, it will be apparent to those skilled in the art that variations and modifications are possible without deviating from the broad spirit and principle of the invention that shall be limited solely by the scope of the claims appended hereto.

What is claimed is:

1. A spinal stimulation electrode assembly comprising:
   at least one wire lead having a proximal end adapted to couple to an electrical signal generator;

a lamina hook having a blade hooking in a hooking direction;

an electrode adapted to telescope from the blade in the hooking direction and having at least one electrical contact formed thereon that is electrically coupled to the wire lead; such that when the hook is disposed on a lamina of a spine and the electrode is telescoped from the blade, the electrical contact is positioned adjacent the spinal cord and an application of an electrical signal to the proximal end of the wire lead causes an electric potential to be applied to the spinal cord.

2. The assembly of claim 1, wherein the blade has a bore extending therethrough and the electrode is adapted to telescope from the bore.

3. The assembly of claim 1, further comprising an electrode lock that can be used to lock the electrode in a telescoped position.

4. The assembly of claim 3, wherein the electrode lock comprises a rough surface on the electrode, a rough surface on the bore, and a cap having a rough surface that frictionally engages the electrode's rough surface and causes the bore's rough surface to frictionally engage the electrode's rough surface when the cap is closed.

5. The assembly of claim 1, wherein the hook further comprises a head that can be used to couple the hook to a bone of the spine when the hook is disposed on the lamina.

6. The assembly of claim 5, wherein the head comprises a hole through which a wire may be passed and tied to the bone.

7. The assembly of claim 1, wherein:

the wire lead comprises a plurality of wire leads and is encased in an insulating and flexible elastomeric sheath;

the electrical contact comprises a plurality of electrical contacts; and the hook comprises an insulating and flexible elastomeric coating.

8. A spinal stimulation electrode assembly comprising:

first and second wire leads each having a proximal end adapted to couple to an electrical signal generator;

a lamina hook having a blade hooking in a hooking direction;

a first electrode adapted to telescope from the blade in the hooking direction and having at least one electrical contact formed thereon that is electrically coupled to the first wire lead;

a second electrode adapted to telescope from the blade in an opposite direction from the hooking direction and having at least one electrical contact formed thereon that is electrically coupled to the second wire lead; such that when the hook is disposed on a lamina of the spine and the first and second electrodes are telescoped from the blade, the electrical contacts are positioned adjacent the spinal cord and an application of electrical signals to the proximal ends of the wire leads causes electric potentials to be applied to the spinal cord.

9. The assembly of claim 8, wherein the blade has a forked bore extending therethrough and the first electrode is adapted to telescope from a first branch of the bore and the second electrode is adapted to telescope from a second branch of the bore.

10. The assembly of claim 9, further comprising an electrode lock that can be used to lock the electrodes in their respective telescoped positions.

11. The assembly of claim 10, wherein the electrode lock comprises a rough surface on the first electrode, a rough surface on the second electrode, a rough surface on the bore, and a cap having a rough surface that frictionally engages one of the rough surfaces of the electrodes and causes the bore's rough surface to frictionally engage the other of the rough surfaces of the electrodes, and the rough surfaces of the electrodes to frictionally engage one another when the cap is closed.

12. The assembly of claim 8, wherein the hook further comprises a head that can be used to couple the hook to a bone of the spine when the hook is disposed on the lamina.

13. The assembly of claim 12, wherein the head comprises a hole through which a wire may be passed and tied to the bone.

14. The assembly of claim 8, wherein:

each of the first wire lead and the second wire lead comprises a plurality of wire leads and is encased in an insulating and flexible elastomeric sheath;

each of the electrical contact of the first electrode and the electrical contact of the second electrode comprises a plurality of electrical contacts; and the hook comprises an insulating and flexible elastomeric coating.

15. A spinal stimulation electrode assembly comprising:

first and second wire leads each having a proximal end adapted to couple to an electrical signal generator;

a lamina hook having a blade hooking in a hooking direction, the blade having an undersurface that seats adjacent to a spinal cord when the hook is disposed on a lamina of a spine, the undersurface having at least one electrical contact formed thereon that is electrically coupled to the first wire lead;

an electrode adapted to telescope from the blade in an opposite direction from the hooking direction and having at least one electrical contact formed thereon that is electrically coupled to the second wire lead; such that when the hook is disposed on a lamina of a spine and the electrode is telescoped from the blade, the electrical contacts are positioned adjacent the spinal cord and an application of electrical signals to the proximal ends of the wire leads causes electric potentials to be applied to the spinal cord.

16. The assembly of claim 15, wherein the blade has a bore extending therethrough and the electrode is adapted to telescope from the bore.

17. The assembly of claim 16, further comprising an electrode lock that can be used to lock the electrode in a telescoped position.

18. The assembly of claim 17, wherein the electrode lock comprises a rough surface on the electrode, a rough surface on the bore, and a cap having a rough surface that frictionally engages the electrode's rough surface and causes the bore's rough surface to frictionally engage the electrode's rough surface when the cap is closed.

19. The assembly of claim 15, wherein the hook further comprises a head that can be used to couple the hook to a bone of the spine when the hook is disposed on the lamina.

20. The assembly of claim 15, wherein:

each of the first wire lead and the second wire lead comprises a plurality of wire leads and is encased in an insulating and flexible elastomeric sheath;

each of the electrical contact of the undersurface and the electrical contact of the electrode comprises a plurality of electrical contacts; and the hook comprises an insulating and flexible elastomeric coating.

* * * * *